United States Patent
Raiford et al.

(10) Patent No.: US 6,297,304 B1
(45) Date of Patent: Oct. 2, 2001

(54) FLUORINATED DIESTER MELT ADDITIVES FOR THERMOPLASTIC POLYMERS

(75) Inventors: Kimberly Gheysen Raiford, Hockessin; Theodor Arthur Liss, Wilmington; Edward James Greenwood, Hockessin; Jack Robert Kirchner, Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/336,954

(22) Filed: Jun. 21, 1999

Related U.S. Application Data

(62) Division of application No. 08/856,627, filed on May 14, 1997, now Pat. No. 5,977,390, which is a continuation of application No. 08/579,044, filed on Dec. 21, 1995, now abandoned.

(51) Int. Cl.$^7$ ....................................................... C08J 5/10
(52) U.S. Cl. ........................................... 524/307; 525/344
(58) Field of Search ............................... 524/307; 525/344

(56) References Cited

U.S. PATENT DOCUMENTS

| | | | | |
|---|---|---|---|---|
| 3,686,281 | * | 8/1972 | Knell et al. ........................... | 260/475 |
| 3,716,401 | | 2/1973 | Axelrod ........................ | 117/138.8 UA |
| 3,957,672 | * | 5/1976 | Zisman et al. ......................... | 252/171 |
| 4,029,585 | | 6/1977 | Dettre et al. ........................... | 252/8.6 |
| 5,145,727 | | 9/1992 | Potts et al. ............................ | 428/198 |
| 5,149,576 | | 9/1992 | Potts et al. ............................ | 428/198 |
| 5,178,931 | | 1/1993 | Perkins et al. ........................ | 428/198 |
| 5,178,932 | | 1/1993 | Perkins et al. ........................ | 428/198 |

FOREIGN PATENT DOCUMENTS

| | | | |
|---|---|---|---|
| 22 39 709 A | 2/1973 | (DE) . | |
| 63 045 238 A | 2/1988 | (JP) . | |
| 3041160 | 2/1991 | (JP) . | |
| 5148454 | 6/1993 | (JP) . | |
| 07 330 673 A | 12/1995 | (JP) . | |
| 08 259 482 A | 10/1996 | (JP) . | |
| 08 259 501 A | 10/1996 | (JP) . | |
| 08 269 342 A | 10/1996 | (JP) . | |
| WO 92/18569 | 10/1992 | (WO) .............................. | C08L/23/06 |
| WO 95/01396 | 1/1995 | (WO) .............................. | C08L/23/04 |

* cited by examiner

*Primary Examiner*—Peter D. Mulcahy

(57) ABSTRACT

Fluorinated diesters useful for imparting repellency of low surface tension fluids to thermoplastic polymers of formulae $R_f$—O—C(O)—$(CH_2)_n$—C(O)—O—$R_1$;

$R_f$—O—C(O)—$CH_2$—CH($R_2$)—C(O)—O—$R_f$;

a mixture of $R_f$—O—C(O)—$(CH_2)_n$—C(O)—O—$R_1$, $R_f$—O—C(O)—$(CH_2)_n$—C(O)—$R_f$, and $R_1$—O—C(O)—$(CH_2)_n$—C(O)—O—$R_1$;

and $[F(CF_2)_x CH_2 CH_2$—S—$CH_2]_2$—C—$[CH_2$—O—C(O)—$C_{17}H_{35}]_2$;

wherein $R_f$ is $F(CF_2)_x$—$(CH_2)_m$ wherein x is 4 to 20 and m is 2 to 6, or $F(CF_2)_x$—$SO_2 N(R_3)$—$R_4$ wherein x is 4 to 20; $R_1$ is a saturated aliphatic hydrocarbon with an average carbon chain length of 12 to 66 carbons; $R_2$ is a saturated or unsaturated hydrocarbon with 1–20 carbon atoms; $R_3$ is an alkyl radical having 1 to 4 carbon atoms; $R_4$ is an alkylene radical having 1 to 12 carbon atoms; n is 1 to 20, and x is 4 to 20 are disclosed.

3 Claims, No Drawings

FLUORINATED DIESTER MELT ADDITIVES FOR THERMOPLASTIC POLYMERS

This is a division of application Ser. No. 08/856,627 filed May 14, 1997, now U.S. Pat. No. 5,977,390 which is a continuation of application Ser. No. 08/579,044 filed Dec. 21, 1995, now abandoned.

FIELD OF THE INVENTION

This invention relates to certain fluorinated diesters and to a process for imparting superior repellency of low surface tension fluids to thermoplastic polymers, in particular fibers, fabrics, nonwovens, films, and molded articles by the addition of the diesters to the polymer melt.

BACKGROUND OF THE INVENTION

Thermoplastic polymer fibers are frequently treated with fluorochemical compounds in order to affect the surface characteristics of the fiber, for example to improve water repellency or to impart stain or dry soil resistance. Most frequently, fluorochemical dispersions are applied topically to the fabrics made from these fibers by spraying, padding or foaming, followed by a drying step to remove water.

For example, a method is known for obtaining dry soil resistance and nonflame propagating characteristics in a textile fiber by applying topically aqueous dispersions of a variety of fluorinated esters derived from perfluoroalkyl aliphatic alcohols of the formula $C_nF_{2n+1}(CH_2)_mOH$ where n is from about 3 to 14 and m is 1 to 3, together with mono- or polycarboxylic acids which contain from 3 to 30 carbons and can contain other substituents. The fluorinated esters include, among others, a perfluoroalkylethyl stearate corresponding to "ZONYL" FTS, as well as perfluoroalkylethyl diesters made from dodecanedioic acid or tridecanedioic acid.

It is well recognized that the process of manufacturing thermoplastic polymeric fibers and fabrics could be simplified and significant capital investment could be eliminated if the topical application were replaced by incorporating a fluorochemical additive into the polymer melt prior to the extrusion of the fiber. The difficulty has been in finding suitably effective fluorochemical additives.

Thermoplastic polymers include, among others, polyolefins, polyesters, polyamides and polyacrylates. Polyolefins, and in particular polypropylene, are frequently used for disposable nonwoven protective garments, particularly in the medical/surgical field, in part because of a polyolefin's inherent water-repellency. However, polyolefins are not inherently good repellents for other lower surface tension fluids frequently encountered in the medical field such as blood and isopropyl alcohol. To get around this deficiency, fluorochemical dispersions are applied topically to these fabrics.

The requirements of an additive suitable for incorporating into a polyolefin melt include, besides the ability to repel low surface tension fluids at a low concentration of the additive, a satisfactory thermal stability and low volatility to withstand processing conditions. Preferably the compound will migrate to the surface of the fiber so as to minimize the amount of additive needed for adequate repellency. While this migration can often be enhanced by post-extrusion heating of the fiber, it is more preferable for the migration to occur without the need for this heating step. This requirement for mobility in the polymeric fiber in turn tends to limit the size of the fluorochemical molecule, and effectively eliminates from consideration high molecular weight polymeric fluorochemical additives.

The general concept of incorporating fluorochemical additives into a polyolefin fiber melt is known, but the difficulty in finding suitable effective additives has limited the application of this concept. Many of the past efforts to evaluate such fluorochemical additives have been aimed at improving other properties of the polyolefin, and do not teach methods of improving its repellency to low surface tension fluids.

Nonwoven composite structures are known consisting in part of two or more melt-extruded nonwoven layers, at least one of which includes an additive which imparts to the surface at least one characteristic different than the surface characteristics of the polymer alone as a result of preferential migration of the additive to the surface without the need for post-formation treatment of any kind. Examples of the additive-including layer include polypropylene modified by commercially available fluorochemical additives, including "ZONYL" FTS defined above.

U.S. Pat. No. 5,178,931 and U.S. Pat. No. 5,178,932 disclose specific nonwoven laminiferous and composite structures respectively, consisting in part of three melt-extruded nonwoven layers, the second of which includes an additive which imparts alcohol repellency as a result of preferential migration of the additive to the surface without the need for post-formation treatment of any kind, and where at least one of the first and third layers has been treated by topical application of an agent to change its characteristics in some way. Examples of the additive included in the second layer include commercially available fluorochemicals, including "ZONYL" FTS.

Soil resistant polymeric compositions are known which are prepared by melt extrusion with a nonpolymeric fluorochemical dispersed throughout the polymer. The polymers used include polypropylene, polyethylene, polyamide and polyester, and the fluorochemical used is a perfluoroalkylstearate, in particular "ZONYL" FTS.

Japanese Patent Application 3-41160 to Kao Corp. teaches a thermoplastic resin composition containing a long chain fatty ester containing a perfluoroalkyl group of the formula $R_f\text{—}R_1\text{—}OCO\text{—}R_2$ wherein $R_f$ is a perfluoroalkyl group with 5 to 16 carbons, $R_1$ is an alkylene group with 1 to 4 carbons, and $R_2$ is an unsaturated alkyl group or a saturated alkyl group with 21 to 50 carbons. The resins included polyethylene and polypropylene. Benefits of the additive were shown by the contact angle of water with molded articles of the resin. No tests were reported on the repellency of resulting polymers to low surface tension fluids.

In summary, while the prior art discloses numerous examples of polyolefin fibers containing a fluorochemical additive incorporated at the melt stage to alter the surface characteristics of the extruded fiber, much of this is directed at soiling and staining resistance or water repellency. Those references which disclose imparting alcohol repellency to polyolefin fabrics employ "ZONYL" FTS. A need exists to achieve superior repellency to low surface tension fluids and superior product efficiency. The fluorinated compounds of the present invention meet this need.

SUMMARY OF THE INVENTION

The present invention comprises a compound of formula A $$R_f\text{—}O\text{—}C(O)\text{—}(CH_2)_n\text{—}C(O)\text{—}O\text{—}R_1 \qquad A$$

wherein $R_f$ is selected from the group consisting of
1) $F(CF_2)_x$—$(CH_2)_m$ wherein x is from about 4 to about 20, and m is from about 2 to about 6; and
2) $F(CF_2)_x$—$SO_2N(R_3)$—$R_4$ wherein x is a positive integer of from about 4 to about 20; $R_3$ is an alkyl radical of from about 1 to about 4 carbon atoms; and $R_4$ is an alkylene radical of from about 1 to about 12 carbon atoms;

and wherein $R_1$ is a saturated aliphatic hydrocarbon having from about 12 to about 66 carbon atoms; and n is 1 to about 20.

The present invention further comprises a compound of formula B

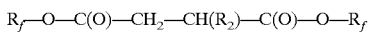  B wherein each $R_f$ is independently selected from the group consisting of
1) $F(CF_2)_x$—$(CH_2)_m$ wherein x is from about 4 to about 20, and m is from about 2 to about 6; and
2) $F(CF_2)_x$—$SO_2N(R_3)$—$R_4$ wherein x is a positive integer of from about 4 to about 20; $R_3$ is an alkyl radical of from about 1 to about 4 carbon atoms; and $R_4$ is an alkylene radical of from 1 to about 12 carbon atoms;

and wherein $R_2$ is a saturated or unsaturated hydrocarbon having from 1 to about 30 carbon atoms.

The present invention further comprises a mixture C comprising:
1) at least one compound of formula A

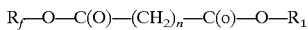  A 2) at least one compound of formula D

  D 3) at least one compound of formula E

  E wherein each $R_f$ is independently selected from the group consisting of
a) $F(CF_2)_x$—$(CH_2)_m$ wherein x is from about 4 to about 20, and m is from about 2 to about 6; and
b) $F(CF_2)_x$—$SO_2N(R_3)$—$R_4$ wherein x is a positive integer of from about 4 to about 20; $R_3$ is an alkyl radical of from 1 to about 4 carbon atoms; and $R_4$ is an alkylene radical of from 1 to about 12 carbon atoms;

and wherein each $R_1$ is independently a saturated aliphatic hydrocarbon having from about 12 to about 66 carbon atoms; and each n is independently 1 to about 20.

The present invention further comprises a compound of formula F

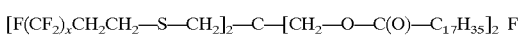 F wherein x is from about 4 to about 20.

The present invention further comprises a composition comprising 1) at least one of the compound of formula A, the compound of formula B, the mixture C, or the compound of formula F, each as defined above, and 2) at least one thermoplastic polymer.

The present invention further comprises a filament, fiber, film, molded article, or nonwoven web or fabric each comprising 1) at least one thermoplastic polymer and 2) at least one compound of formula A, compound of formula B, mixture C, or compound of formula F, each said compound or said mixture as defined above.

The present invention further comprises a process for imparting superior repellency of low surface tension fluids to thermoplastic polymer articles of manufacture comprising forming a mixture prior to article formation of a polymer and an effective amount of an additive selected from the group consisting of a compound of formula A, a compound of formula B, a mixture C, or a compound of formula F, or mixtures thereof, as defined above, and melt extruding the mixture. This process is particularly suitable for imparting repellency of low surface tension fluids to polyolefin articles, and may be used either with or without post-extrusion heating of the article to promote movement of the additive to the article surface. The term "article" as used herein includes filaments, fibers, nonwoven webs or fabrics, films or molded articles.

DETAILED DESCRIPTION OF THE INVENTION

Superior repellency to low surface tension fluids is imparted to thermoplastic polymer articles, such as filaments, fibers, nonwovens, fabrics, films, or molded articles, by the addition of certain novel monomeric fluorinated diester compounds to a polymer prior to article formation and melt extruding the resulting mixture. This process is used either with or without post-extrusion heating of the article to promote movement of the additive to the article surface, since the diester compounds of this invention tend by their nature to concentrate on the surface.

The term "low surface tension fluids" is used herein to mean fluids having a surface tension of less than 50 dynes/cm ($50 \times 10^{-7}$ newton meter). Examples of such fluids include alcohols, blood and certain body fluids.

The compounds of the present invention comprise the following groups of fluorinated diester compounds:

I. Fluorocarbon/hydrocarbon diesters of the formula A:

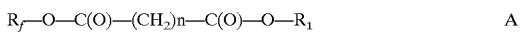 A

II. Bis-fluorocarbon esters of the formula B:

 B,

III. Mixture C comprising the diesters of formula A, the bis-esters of the fluorocarbon moieties of formula A represented by formula D, and the bis-esters of the hydrocarbon moieties of formula A represented by formula E.

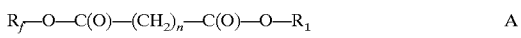 A

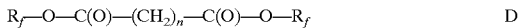 D

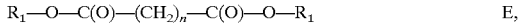 E, and

IV. Distearyl fluorocarbon esters of the formula F:

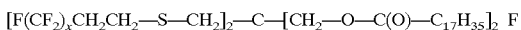 F

In the compounds and mixtures of this invention, $R_f$ in the above formulae is $F(CF_2)_x$—$(CH_2)_m$ wherein x has a range of about 4 to about 20, and preferably an average value of from about 7 to about 10, and m has a value of 2 to 6. Especially preferred for $R_f$ is a composition wherein the chain length distribution is as follows:

x=6 or less, 0–10% by weight
x=8, 45–75% by weight x=10, 20–40% by weight
x=12, 1–20% by weight
x=14 or greater, 0–5% by weight.

This composition range, when m=2, is hereinafter referred to as Telomer BN. This definition of $R_f$ in the formula $R_f$—OH is referred to as Telomer BN alcohol.

Alternatively in this invention, $R_f$ is a fluorinated sulfonamide of the structure $F(CF_2)_x$—$SO_2N(R_3)$—$R_4$ wherein x is a positive integer from about 4 to about 20, preferably 4 to 10 inclusive; $R_3$ is an alkyl radical having from 1 to about 4 carbon atoms; and $R_4$ is an alkylene radical having from 1 to about 12 carbon atoms. Preferably $R_3$ is $CH_3$ and $R_4$ is —$CH_2CH_2$—, —$(CH_2)_3$—or —$(CH_2)_4$—.

The fluoroalkyl portion of the alternative $R_f$ structures is a fluorinated, preferably saturated, monovalent, non-aromatic, aliphatic radical of at least three fully fluorinated connected carbon atoms in a chain. The chain in the radical is straight, branched, or, if sufficiently large, cyclic and is optionally interrupted by divalent oxygen atoms, hexavalent sulfur atoms or trivalent nitrogen atoms bonded only to carbon atoms. A fully fluorinated aliphatic radical is preferred, but hydrogen or chlorine atoms are optionally present as substituents in the radical provided that not more than one atom of either is present in the radical for every two carbon atoms.

$R_1$ is a saturated aliphatic hydrocarbon with an average carbon chain length of from about 12 to about 66 carbons, preferably from about 24 to about 50 carbons. Alcohols corresponding to $R_1$—OH are commercially available from Petrolite Corporation, Polymers Division Headquarters, 6910 E. 14th Street, Tulsa, Okla., U.S.A. 74112 under the trademark "UNILIN". "UNILIN" alcohols are fully saturated, long-chain linear alcohols. The approximate $R_1$ carbon atom ranges of "UNILIN" 350, 425, 550 and 700 are 12 to 50, 14 to 58, 16 to 56 and 14 to 66, respectively. The average chain lengths for "UNILIN" 350, 425, 550 and 700 are about 24, 32, 40 and 48, respectively. These are preferred for use in the present invention. More particularly the "UNILIN" carbon chain lengths are as noted in Table A:

TABLE A

| UNILIN | Lit. Avg.* | % Alcohol | GC DATA** Range | Average |
|---|---|---|---|---|
| 350 | C24–26 |  | C12–46 | C24–26 |
| 425 | C30–32 | 85.0 | C14–58 | C30–32 |
| 550 | C40–42 | 79.5 | C16–56 | C38 |
| 700 | C48–50 | 83.6 | C14–66 | C50 |

*Literature average
**Gas chromatography data $R_2$ in formula B is a saturated or unsaturated hydrocarbon having from 1 to about 30 carbon atoms. Preferably $R_2$ is a straight or branched chain hydrocarbon of 12–18 carbon atoms and is saturated or mono-unsaturated. In the above formulas A, D and E, n has a value of 1 to about 20. In formula F, x is from about 4 to about 20.

There are various methods by which the above compounds can be prepared, and the inventive process is not limited to a particular method of preparation. For example, the compounds of formula A are conveniently made by reacting an appropriate fatty alcohol with the anhydride of an appropriate diacid to form an acid ester, which is first converted to the acid chloride and then reacted with an appropriate fluorinated alcohol. With this reaction sequence, the end product will have a fluorocarbon tail on one end of the molecule and a hydrocarbon tail on the other end, i.e substantially no diesters will have two fluorocarbon tails or two hydrocarbon tails. The compounds of formula B are conveniently made by reacting an appropriately substituted anhydride of a diacid with about 2 equivalents of an appropriate fluorinated alcohol. The compounds in mixture C are conveniently made by simultaneously reacting an appropriate diacid with one equivalent of the appropriate fluorinated alcohol and one equivalent of an appropriate fatty alcohol, or by sequentially reacting an anhydride of an appropriate diacid with the above two alcohols in either order.

The compounds of formula F are prepared by reacting stearic acid and a diol having the following structure:

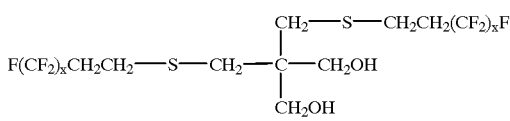

Other compounds in these groups can readily be made by those skilled in the art by following similar processes.

The compounds and mixture of this invention are mixed with thermoplastic polymers by adding them to granular, pelletized, powdered or other appropriate forms of the polymers and rolling, agitating or compounding the mixture to achieve a uniform mixture which is then melt extruded. Alternatively the compounds of this invention are added to a polymer melt to form a mixture which is then melt extruded. The thermoplastic polymer is a polyolefin, polyester, polyamide, or polyacrylate. Preferably the thermoplatic polymer is a polyolefin, mixture or blend of one or more polyolefins, a polyolefin copolymer, mixture of polyolefin copolymers, or a mixture of at least one polyolefin and at least one polyolefin copolymer. The thermoplastic polymer is more preferably a polyolefin polymer or copolymer wherein the polymer unit or copolymer unit is ethylene, propylene or butylene or mixtures thereof. Thus the polyolefin is preferably polyethylene, polypropylene, polybutylene or a blend of copolymers thereof.

The amount of the fluorinated compound added to the thermoplastic polymer is preferably between 0.1 and 5% by weight of the polymer. Amounts above this range can be used but are unnecessarily expensive in relation to the benefit received. Below this range the benefit is too small for practical use. The blend is then melted and extruded into filaments, fibers, nonwoven fabrics or webs, films or molded articles using known methods. The fluorine content of the filament, fiber, nonwoven web or fabric prepared from said filament or fiber, film, or molded article is from about 200 μg/g to about 25,000 μg/g.

Extrusion is used to form various types of nonwovens. In particular, extrusion is used to form a melt blown nonwoven web of continuous and randomly deposited microfibers having an average diameter of approximately 0.1 to 10 microns, preferably in the range of about 3 to 5 microns. The melt extrusion is carried out through a die at a resin flow rate of at least 0.1 to 5 grams per minute per hole, with the microfibers being randomly deposited on a moving support to form the web.

In the above melt blowing process, polymer and a compound of the percent invention are fed into an extruder where it is melted and passed through a die containing a row of tiny orifices. As the polymer emerges from the die, it is contacted by two converging, high-velocity hot air streams, which attenuate the polymer into a blast of fine, discontinuous fibers of 0.1 to 10 microns in diameter. The useful polymer throughputs or flow rates range from 0.1 to 5 grams per minute per hole. Typical gas flow rates range from 2.5–100 psi ($1.72 \times 10^5$ to $6.89 \times 10^5$ Pa) per minute of gas outlet area. The air temperature ranges from 400° F.(204° C.) to 750° F.(399° C.) Cooling air then quenches the fibers, and they are deposited as a random, entangled web on a moving screen which is placed 6–12 inches (15.2–30.5 cm) in front of the blast of fibers.

Melt blowing processes are described in further detail in articles by V. A. Wente, "Superfine Thermoplastic Fibers", Industrial and Engineering Chemistry, Vol. 48(8), pp 1342–1346 (1956); and by R. R. Buntin and D. T. Lohkamp, "Melt Blowing—A One—step Web Process for New Nonwoven Products", Journal of the Technical Association of the Pulp and Paper Industry, Vol. 56(4), pp 74–77 (1973); as well as in U.S. Pat. No. 3,972,759 to R. R. Buntin. The disclosures of these documents are hereby incorporated by reference.

The unique properties of a melt blown nonwoven web comprised of a random array of fine, entangled fibers include very large surface areas, very small pore sizes, moderate strength and light weight fabric structure. These properties make the nonwoven webs particularly suitable for such applications as medical fabrics where barrier properties as well as breathability and drape are important.

Extrusion is used to form polymeric films. In film applications, a film-forming polymer and a compound of the present invention are simultaneously melted and mixed as they are conveyed through the extruder by a rotating screw or screws and then forced out through a slot or flat die, for example, where the film is quenched by a variety of techniques known to those skilled in the art. The films optionally are oriented prior to quenching by drawing or stretching the film at elevated temperatures.

Molded articles are produced by pressing or injecting molten polymer containing a compound of the present invention from a melt extruder as described above into a mold where the polymer solidifies. Typical melt forming techniques include injection molding, blow molding, compression molding and extrusion, and are well known to those skilled in the art. The molded article is then ejected from the mold and optionally, heat-treated to effect migration of the polymer additives to the surface of the article.

An optional heating or annealing step can be conducted but is not required. The polymer melt or extruded fiber, filament, nonwoven web or fabric, film, or molded article is heated to a temperature of from about 25° C. to about 150° C. The heating in some cases may improve the effectiveness of the fluorochemical additive in imparting alcohol repellency.

The compounds, mixtures, and compositions of the present invention are useful in various filaments, fibers, nonwoven webs or fabrics, films and molded articles. Examples include fibers for use in fabrics and carpets, nonwoven fabrics used in protective garments used in the medical/surgical field, and molded plastic articles of many types. The process of the present invention is useful for imparting repellency of low surface tension fluids to various thermoplastic polymer articles such as filaments, fibers, nonwoven webs or fabrics, films and molded articles.

EXAMPLES

Example 1

Synthesis of $R_f$—O—C(O)—$(CH_2)_n$—C(O)—O—$R_1$, wherein $R_f$ is an aliphatic fluorocarbon radical of formula $F(CF_2)_x(CH_2)_m$ where the average value of x is 9, m=2, n=2, and wherein $R_1$ has an average value of 24 carbon atoms.

Step A

A 2-liter 4-necked flask was equipped with mechanical agitation, a temperature control device, Dean-Stark trap, water condenser, and nitrogen gas inlet and outlet tubes. It was charged with 600 mL of toluene which was then heated at reflux for one hour to remove traces of water. After the toluene was cooled, 103.2 g (1.0 mole) succinic anhydride and 435.0 g (1.0 mole) "UNILIN" 350 alcohol were added. The mixture was heated at reflux for 4 hours and cooled. The toluene was removed by rotary evaporation. The product was dried in a vacuum oven at 50° C. for 18 hours yielding 532.8 g (99% yield) of white waxy solid.

Step B

A dry 5-liter 4-necked flask was equipped with mechanical agitation, temperature control device and a water condenser fitted with a drying tube connected to both a nitrogen gas inlet tube and caustic scrubber with a nitrogen gas outlet. It was charged with 403.4 g (0.754 mole) $H(CH_2)_{24}$—O—C(O)—$(CH_2)_2$—COOH from Step A, 3 L of 1,2—dichloroethane, 2.5 g (0.011 mole) benzyltriethylammonium chloride and 55 mL (0.754 mole) thionyl chloride. The reaction mixture was heated at reflux for 3 hours, and after being cooled to 70° C., 397.4 g (0.754 mole) of Telomer BN alcohol was added. The reaction mixture was then cooled to 35° C. and 87.7 g (0.867 mole) of triethylamine was added dropwise over 2 hours. After the addition was complete, the mixture was held at 35° C. for 3 hours and then heated at 60° C. for 1 hour. At room temperature, the reaction mixture was filtered and the solid product air—dried, slurried in 5 L isopropyl alcohol at 60° C. for 1 hour, filtered, and washed with deionized water and with isopropyl alcohol. The product was recrystallized in portions from isopropyl alcohol yielding 447.1 g (57% yield) off-white solid; m.p. 83.8° C. by DSC (Differential Scanning Calorimetry). The percent fluorine found was 32.5%; the percent fluorine calculated was 33.9%.

Example 2

Synthesis of $R_f$—O—C(O)—$CH_2$—CH($CH_2CH$=$CHC_{15}H_{31}$)—C(O)—O—$R_f$, where $R_f$ is an aliphatic fluorocarbon radical of formula $F(CF_2)_x(CH_2)_m$ where the average value of x is 9, and m=2.

A 250-mL flask was equipped with mechanical agitation, a temperature control device, water condenser, Dean-Stark trap and nitrogen gas inlet and outlet tubes.

It was charged with 28.3 g (0.08 mole) octadecenylsuccinic anhydride (acid # 317.4 mg KOH/g cmpd), 84.2 g (0.16 mole) Telomer BN alcohol, 0.2 g phosphorous acid (70%) and 0.08 g boric acid. The mixture was heated at 140–145° C. for approximately 48 hours. A tan, waxy solid was isolated weighing 102.1 g (91.9% yield); m.p. 42.4° C. (by DSC); percent fluorine found was 49.2%; percent fluorine calculated was 50.9%.

Example 3

Synthesis of mixture of $R_f$—O—C(O)—$(CH_2)_n$—C(O)—O—$R_1$, $R_f$—O—C(O)—$(CH_2)_n$—C(O)—O—$R_f$, and $R_1$—O—C(O)—$(CH_2)_n$—C(O)—O—$R_1$, where $R_f$ is an aliphatic fluorocarbon radical of formula $F(CF_2)_x(CH_2)_m$ where the average value of x is 9, m=2, n=10, and $R_1$ has an average value of 24 carbon atoms.

The apparatus of Example 2 was charged with 43.5 g (0.1 mole) UNILIN 350 alcohol, 61.0 g (0.11 mole) Telomer BN alcohol, 23.0 g (0.1 mole) 1,12-dodecanedioic acid, 0.5 g 70% phosphorous acid and 0.2 g boric acid. The mixture was heated at 140° C. for approximately 150 hours. A tan waxy solid was isolated, m.p. 61.8° C. (by DSC); percent fluorine found 31.8, percent fluorine calculated 34.0%.

Example 4

Synthesis of a mixture similar to that in Example 3 except that an alternative preparative method was used, and that n=2.

Step A

A 1-liter 4-necked flask was equipped with mechanical agitation, a temperature control device, water condenser, Dean-Stark trap and nitrogen gas inlet and outlet tubes. It was charged with 300 mL toluene, 41.3 g (0.4 mole) succinic anhydride (97%) and 210.8 g (0.4 mole) Telomer BN alcohol. The mixture was heated at reflux for 4 hours and then cooled to 60° C. The toluene was removed by rotary evaporation, and the off-white solid product was dried in a vacuum oven at 50° C. for approximately 18 hours yielding 225.1 grams (89.3% yield).

Step B

A 100 mL 4-necked flask was equipped with mechanical agitation, a temperature control device, water condenser, Dean-Stark trap and nitrogen gas inlet and outlet tubes. It was charged with 60.5 g (0.1 mole) $F(CF_2)_x(CH_2)_2$—OC(O)—$(CH_2)_2$—COOH from Step A above, 43.5 g (0.1 mole) "UNILIN" 350 alcohol, 0.2 g 70% phosphorous acid and 0.08 g boric acid. The reaction mixture was heated at 140° C. for approximately 48 hours. A tan waxy solid was recovered, m.p. 50.5° C. (by DSC); percent fluorine found was 33.2%, percent fluorine calculated was 35.3%.

Example 5

Step 1: Preparation of the Polymer Blend

Uniform mixtures of the fluorochemical additives produced in Examples 1 through 4 together with a polyolefin were prepared by combining them and rolling the mixture for 24 hours. The polyolefin used was Escorene PD3545G or PD3746G (Exxon Chemical Americas, P.O. Box 3273, Houston, Tex. 77001) polypropylene resin having a melt flow rate of approximately 800 and 1,000 respectively). The composition and calculated fluorine concentrations of the mixtures are given in the Table 1. Two comparative examples using compounds described in prior art were prepared in a similar manner. Comparative Example 1 used the mono-ester "ZONYL" FTS; Comparative Example 2 used the bis-fluorocarbon ester made from Telomer BN alcohol and dodecanedioic acid.

TABLE 1

| Example # | Additive (g) | Polyolefin (g) | ppm F calc'd |
|---|---|---|---|
| 1 | 14.1 | 1348 | 0.330 |
| 2 | 11.1 | 1351 | 0.400 |
| 3 | 16.0 | 1346 | 0.373 |
| 4 | 17.6 | 1344 | 0.429 |
| Comp. Ex. 1 | 16.2 | 1800 | 0.400 |
| Comp. Ex. 2 | 2.2 | 452 | 0.300 |

Step 2: Melt Blown Web Formation

Melt blown nonwoven webs were prepared from the above mixtures using a 6-inch (15 cm) melt blowing pilot unit at a polymer feed rate of about 0.4 gram/minute/hole. The polymer blends were fed into the extruder having three barrel zones at temperatures ranging from 175° C. to 250° C. The temperature at the die was 232 to 254° C. and the air temperature was 260 to 271° C. The die tip gap was 0.060 inches (0.15 cm) and the primary air pressure was 2.6 psi ($17.9 \times 10^3$ Pa). The webs were formed on a drum coated with "TEFLON" and collected on a take-up roll operating at 30 feet/minute (914 cm/minute) which resulted in the fabrics having a basis weight of 1.0 oz./square yard (34 gram/square meter).

Step 3. Repellency Testing

The water repellent properties of the melt blown webs were measured using an isopropyl alcohol/water test and are expressed in terms of percent isopropyl alcohol repellency. Webs that resist penetration of a 100% isopropyl alcohol/0% water solution (lowest surface tension fluid) after 1–2 minutes are given the highest rating of 100. Webs that are only resistant to a 100% water/0% isopropyl alcohol solution after 1–2 minutes are given the lowest rating of 0. Intermediate ratings of 20 to 90 in increments of 10 correspond to solutions of 20% isopropyl alcohol/80% water to solutions of 90% isopropyl alcohol/10% water. The isopropyl alcohol repellency rating for a given fabric corresponds to the lowest surface tension fluid (greatest % isopropyl alcohol/water solution) that does not wet the fabric after 1–2 minutes.

To evaluate in-process repellency, the webs were rated immediately after exiting the melt blown line and then at time intervals of 1 hour, 1 day, 12 days and after heating at 140° F. (60° C.) for 22 hours. Table 2 summarizes the isopropyl alcohol repellency data for the polypropylene melt blown webs containing Examples 1, 2, 3 and 4 and the two comparison examples. Also included in the table is a polypropylene control sample.

TABLE 2

% Isopropyl Alcohol Repellency of Polypropylene Melt Blown Webs

| | | % Repellency | | | | |
|---|---|---|---|---|---|---|
| Example | μg/g Fluorine | In-Process | After 1 Hr | After 1 day | After 12 days | Heated 60° C./22 hr |
| 1 | 3290 | 60–70 | 80 | 90 | 100 | 100 |
| 2 | 3030 | 60–70 | 70 | — | 70 | 70 |
| 3 | 3140 | 30–50 | 60 | 80 | 90 | 90 |
| 4 | 2910 | 50 | 60 | — | 90 | 80 |
| Comp. 1 | 2590 | 30 | 30 | 30 | 60 | 40 |
| Comp. 2 | 1750 | 20 | 20 | 20 | 20 | — |
| Control | | 20 | 20 | 20 | 20 | |

The above results showed the clear advantage of the inventive compositions over the comparative and control samples, the advantages showing up immediately and over time. A related advantage for the inventive compositions was their lower fluorine loss during melt extrusion processing, as shown by comparing the fluorine analyses in the above Table 2 with those in Table 1. The additives in Comparative Examples 1 and 2 showed losses of 35% and 42%, respectively, while the additives in Examples 1, 2, 3 and 4 showed lower fluorine losses of 1%, 24%, 16% and 32%, respectively, contributing to their better performance.

Example 6

A 500-ml round bottom flask equipped with a mechanical agitator, temperature control device, Dean-Stark trap, water condenser, and nitrogen inlet/outlet tubes was charged with 132.5 g (0.11 mole) of a bis(perfluoroalkylethylmercapto) neopentylglycol mixture of the formula $[F(CF_2)_xCH_2CH_2SCH_2]_2C(CH_2OH)_2$, wherein x is predominantly 8, 10 and 12, 78.2 g (0.275 mole) stearic acid, 10 g "AMBERLYST" 15 ion-exchange resin and 80 g 'Baker analyzed' xylenes. The Dean-Stark trap was filled to overflow with xylenes and the reaction flask contents then stirred at reflux. Additional fluoroglycol (10.3 g and 22.3 g, respectively), was added to the reaction mass after 16 hours and 32 hours at reflux.

After a total of 48 hours reflux, the reaction mass was filtered to remove the ion-exchange resin and desolvated by rotary evaporation to recover a 40.5% fluorine content flaky solid.

A polymer blend and melt blown nonwoven web were prepared as in Example 5. Repellency testing was conducted on the web using the procedure detailed in Example 5. The resulting data are summarized in Table 3. These results showed the clear advantage of the inventive compositions of formula F over the comparative examples listed in Table 2.

TABLE 3

| | % Isopropyl Alcohol Repellency of Melt Blown Webs | | | | |
|---|---|---|---|---|---|
| | | % Repellency | | | |
| μg/g fluorine | In process | After 1 hr | After 1 day | After 12 days | Heated |
| 3330 | 80 | 90 | 90 | 90 | 90[1] |
| 1970 | 70 | 70 | — | 90* | 80[2] |
| 1440 | 50 | 50 | — | 80* | 70[2] |

*after 3 days
[1] 140° F. (60° C.)/22 hr.
[2] 176° F. (80° C.) 15 sec.

What is claimed is:

1. A composition for providing repellency to low surface tension fluids comprising at least one thermoplastic polymer selected from the group consisting of polyolefin, polyester, polyamide and polyacrylate, and at least one compound or mixture selected from the group consisting of I) a compound of formula A $$R_f\text{—O—C(O)—(CH}_2)_n\text{—C(O)—O—R}_1 \quad \quad A$$

wherein
Rf is selected from the group consisting of
1) $F(CF_2)_x\text{—}(CH_2)_m$ wherein x is from about 4 to about 20, and m is from about 2 to about 6; and
2) $F(CF_2)_x\text{—SO}_2N(R_3)\text{—R}_4$ wherein x is a positive integer of from about 4 to about 20; $R_3$ is an alkyl radical of from about 1 to about 4 carbon atoms; and $R_4$ is an alkylene radical of from about 1 to about 12 carbon atoms;
$R_1$ is a saturated aliphatic hydrocarbon having from about 12 to about 66 carbon atoms; and n is 1 to about 20;

II) a compound of formula B $$R_f\text{—O—C(O)—CH}_2\text{—CH(R}_2)\text{—C(O)—O—R}_f \quad \quad B$$

wherein
each $R_f$ is as defined above for formula A, and
$R_2$ is a saturated or unsaturated hydrocarbon having from 1 to about 30 carbon atoms;

III) a mixture C comprising
1) at least one compound of formula A $$R_f\text{—O—C(O)—(CH}_2)_n\text{—C(O)—O—R}_1 \quad \quad A$$

2) at least one compound of formula D $$R_f\text{—O—C(O)—(CH}_2)_n\text{—C(O)—O—R}_f \quad \quad D \text{ and}$$

3) at least one compound of formula E $$R_1\text{—O—C(O)—(CH}_2)_n\text{—C(O)—O—R}_1 \quad \quad E$$

wherein
each $R_f$, $R_1$, and n are as defined above for formula A; and

IV) a compound of formula F $$[F(CF_2)_xCH_2CH_2\text{—S—CH}_2]_2\text{—C—}[CH_2\text{—O—C(O)—C}_{17}H_{35}]_2 \quad F$$

wherein x is from about 4 to about 20.

2. The composition of claim 1 wherein the polymer is selected from the group consisting of polyolefin, mixture of polyolefins, polyolefin copolymer, mixture of polyolefin copolymers, and mixture of at least one polyolefin and at least one polyolefin copolymer.

3. The composition of claim 2 wherein the polymer has a polymer or copolymer unit which is ethylene, propylene, butylene, or mixtures thereof.

* * * * *